United States Patent
De Greeve et al.

(10) Patent No.: US 8,830,454 B2
(45) Date of Patent: Sep. 9, 2014

(54) APPARATUS AND METHODS FOR SETTING UP OPTICAL INSPECTION PARAMETERS

(75) Inventors: Johan De Greeve, Lovenjoel (BE); Benjamin Swerts, Deurne (BE)

(73) Assignee: KLA-Tencor Corporation, Milpitas, CA (US)

( * ) Notice: Subject to any disclaimer, the term of this patent is extended or adjusted under 35 U.S.C. 154(b) by 719 days.

(21) Appl. No.: 13/047,587

(22) Filed: Mar. 14, 2011

(65) Prior Publication Data

US 2011/0255081 A1 Oct. 20, 2011

Related U.S. Application Data

(60) Provisional application No. 61/324,590, filed on Apr. 15, 2010.

(51) Int. Cl.
*G06K 9/00* (2006.01)
*G01N 21/00* (2006.01)
*G01N 21/89* (2006.01)

(52) U.S. Cl.
CPC ........ *G01N 21/8901* (2013.01); *G01N 21/8914* (2013.01)
USPC ...................................... 356/237.2; 382/149

(58) Field of Classification Search
USPC ............ 356/237.1–237.5; 382/141, 145, 149; 250/559.44–559.49
See application file for complete search history.

(56) References Cited

U.S. PATENT DOCUMENTS

| | | | |
|---|---|---|---|
| 5,834,661 A * | 11/1998 | Nonaka et al. | 73/866 |
| 6,606,115 B1 * | 8/2003 | Alicandro et al. | 348/164 |
| 7,180,524 B1 * | 2/2007 | Axelrod | 345/593 |
| 7,570,797 B1 * | 8/2009 | Wang et al. | 382/145 |
| 7,693,679 B1 | 4/2010 | Warnke et al. | |
| 8,010,311 B1 * | 8/2011 | Warnke et al. | 702/132 |
| 2002/0122582 A1 * | 9/2002 | Masuda et al. | 382/141 |
| 2003/0133076 A1 * | 7/2003 | Lehmeier et al. | 351/239 |

(Continued)

FOREIGN PATENT DOCUMENTS

| | | |
|---|---|---|
| JP | 2008-509502 | 3/2008 |
| TW | 200940977 A | 10/2009 |

OTHER PUBLICATIONS

WO patent application No. PCT/US2011/031951, International Search Report and Written Opinion mailed Dec. 7, 2011.

(Continued)

*Primary Examiner* — Kara E Geisel
*Assistant Examiner* — Dominic J Bologna
(74) *Attorney, Agent, or Firm* — Kwan & Olynick LLP

(57) ABSTRACT

Provided are novel methods and systems for setting up ranges of optical inspection parameters. These ranges may be later used for inspection of photovoltaic cells for discoloration, for example. A set of values corresponding to an inspection parameter, such as hue, saturation, and intensity, is obtained from a set-up image. The image includes multiple set-up areas, e.g., a defined group of pixels, wherein each set-up area is assigned a corresponding value in the set. A test image is then constructed from multiple test areas that are also associated with the values in the set. Each test area is assigned a color from a set of user defined colors based on the corresponding value and user defined ranges. A user interface includes both a range diagram and test image, which are used to adjust the ranges in the diagram that result in modification of the test image. Adjusting is repeated until the test image meets predetermined criteria.

18 Claims, 6 Drawing Sheets

(56) References Cited

U.S. PATENT DOCUMENTS

| | | |
|---|---|---|
| 2004/0000639 A1* | 1/2004 | Storz .............................. 250/310 |
| 2005/0069083 A1 | 3/2005 | Klingenbeck-Regn |
| 2008/0144905 A1* | 6/2008 | Tallman ........................ 382/131 |
| 2009/0046922 A1* | 2/2009 | Yoshikawa .................... 382/149 |
| 2009/0238444 A1* | 9/2009 | Su et al. ........................ 382/149 |

OTHER PUBLICATIONS

"Chinese Application Serial No. 201180018986, Office Action mailed Mar. 28, 2014", 20 pgs.

"Taiwanese Application Serial No. 100111404, Office Action and Search Report mailed Feb. 21, 2014", 20 pgs.

\* cited by examiner

APPARATUS AND METHODS FOR SETTING UP OPTICAL INSPECTION PARAMETERS

CROSS REFERENCE TO RELATED APPLICATION

This application claims priority to U.S. Provisional Patent Application No. 61/324,590 filed on Apr. 15, 2010, the disclosure of which is incorporated by reference herein in its entirety.

BACKGROUND

Electronic components, such as solar cells, are often inspected for various types of defects using optical inspection systems. For example, inspecting a working surface of a solar cell for discoloration may be used to detect thickness variations of a silicon nitride antireflective coating. Discoloration inspection may involve multiple inspection parameters that need to be individually set up in order to identify certain defects. Some of these defects may be less important and could be generally ignored, while others may be critical and should be carefully screened for. Setting various thresholds of inspection parameters may be used for this purpose.

Discoloration inspection generally has been a manual process in which an operator looks at the solar cell and visually inspects the surface of the cell to judge the quality. Based on the visual quality the operator then can try to manually adjust inspection parameters on a color image in the inspection system. In addition to being subjective, this approach can also be very labor intensive and prone to human mistakes.

SUMMARY

Provided are novel methods and systems for setting up ranges of optical inspection parameters. These ranges may be later used for inspection of photovoltaic cells for discoloration, for example. A set of values corresponding to an inspection parameter, such as hue, saturation, and intensity-value, is obtained from a set-up image. The image includes multiple set-up areas, e.g., a defined group of pixels, such that each set-up area is assigned a corresponding value in the set. A test image is then constructed from multiple test areas that are also associated with the values in the set. Each test area is assigned a color from a set of user defined colors based on the corresponding value and user defined ranges. A user interface includes both a range diagram and test image, which is used to adjust the ranges in the diagram to thereby modify the test image. Adjusting is repeated until the test image meets predetermined criteria.

In certain embodiments, a method for setting up one or more ranges of one or more inspection parameters in an optical inspection system includes the following operations: receiving a set of values corresponding to an inspection parameter, constructing a test image including multiple test areas, displaying the test image and a range diagram on a user interface of the optical inspection system, receiving an adjustment of the limit and/or the nominal limit based on the test image. These operations may be repeated one or more times until the test image reaches predetermined criteria. The received set of values corresponds to set-up areas of a set-up image that could be obtained from an inspected sample. During construction of the test image, locations of the test areas are positioned in such a way that they corresponds to locations of the set-up areas. The colors of the test areas are determined by corresponding values in the set according to following rule. The test areas have the color if the corresponding values in the set fall within the range or the outside color if the corresponding values fall within the outside range. The ranges and the colors are provided in a range diagram. The range diagram corresponds to the inspection parameter and includes a nominal limit and a variation limit. The nominal limit and the variation limit define a range corresponding to the color that does not overlap with an outside range corresponding to the outside color.

In certain embodiments, a range diagram includes a second variation limit defining a second range between the limit described above and the second limit. The additional range does not overlap with the range or the outside range. The additional range corresponds to an additional color that is typically distinct from the color and the outside color described above. The test areas are assigned the additional color if the corresponding values in the set fall within the additional range.

In certain embodiments, a method also includes the following operations: receiving a second set of values of a second inspection parameter, displaying a second range diagram on the user interface, and receiving an adjustment of the second limit and/or the second nominal limit. The second set of values corresponds to the set-up areas. The second range diagram corresponds to the second inspection parameter and includes a second nominal limit and a second limit. The second nominal limit and the second limit define a second range corresponding to a second color that does not overlap with a second outside range corresponding to a second outside color.

In the same or other embodiments, a method may also include operations for constructing a second test image including multiple second test areas such locations of the second test areas corresponds to location of the set-up areas, displaying the second test image, and repeating the displaying and receiving operation for the second test image until the second test image reaches second predetermined criteria. The second test areas are assigned the second color if the corresponding values in the second set fall within the second range. Alternatively, the second outside color is assigned to the second test areas if the corresponding values fall within the second outside range. The adjustment of the second limit and/or the second nominal limit are based on the second test image. The colors of the test areas of the test image may be further determined by corresponding values in the second set. In certain embodiments, a user interface is configured to allow a user to assign other colors to the range and the outside range.

In any of the preceding embodiments, the predetermined criteria may be a balance between the color and the outside color relative to a level of defects present on a sample corresponding to the set-up image. The set-up image may be obtained from a photovoltaic cell. The inspection parameter may be a measure of discoloration, such as hue, saturation, and intensity. A range diagram may be one of the following: a hue circle, a saturation spectrum, and an intensity spectrum.

In certain embodiments, a set of value corresponding an inspection parameter is calculated from corresponding RGB values obtained from the set-up images. The method may also include an operation for obtaining the set-up image from a set-up sample and/or receiving multiple sets of values of the inspection parameter that correspond to multiple set-up images having varying defect levels. Set-up areas can be individual pixels of the set-up image. A nominal limit may be initially set to the most common of all values in the set.

In certain embodiments, a spread of the range remains the same when a limit and/or a nominal limit are being adjusted.

Adjustment may include receiving a numerical input and/or a graphical adjustment of the limit and/or the nominal limit on the range diagram.

In certain embodiments, a computer readable medium containing program instructions for setting up one or more ranges of one or more inspection parameters in an optical inspection system is provided. The computer readable medium may be include computer readable codes for: receiving a set of values corresponding to an inspection parameter, constructing a test image including multiple test areas, displaying the test image and a range diagram on a user interface of the optical inspection system, receiving an adjustment of the limit and/or the nominal limit based on the test image.

In certain embodiments, an optical inspection system for setting up one or more ranges of one or more inspection parameters is provided. The optical inspection system includes at least one memory and at least one processor that are configured to perform the following operations: receiving a set of values corresponding to an inspection parameter, constructing a test image including multiple test areas, displaying the test image and a range diagram on a user interface of the optical inspection system, receiving an adjustment of the limit and/or the nominal limit based on the test image.

These and other aspects of the invention are described further below with reference to the figures.

DETAILED DESCRIPTION OF EXAMPLE EMBODIMENTS

Figure 1:
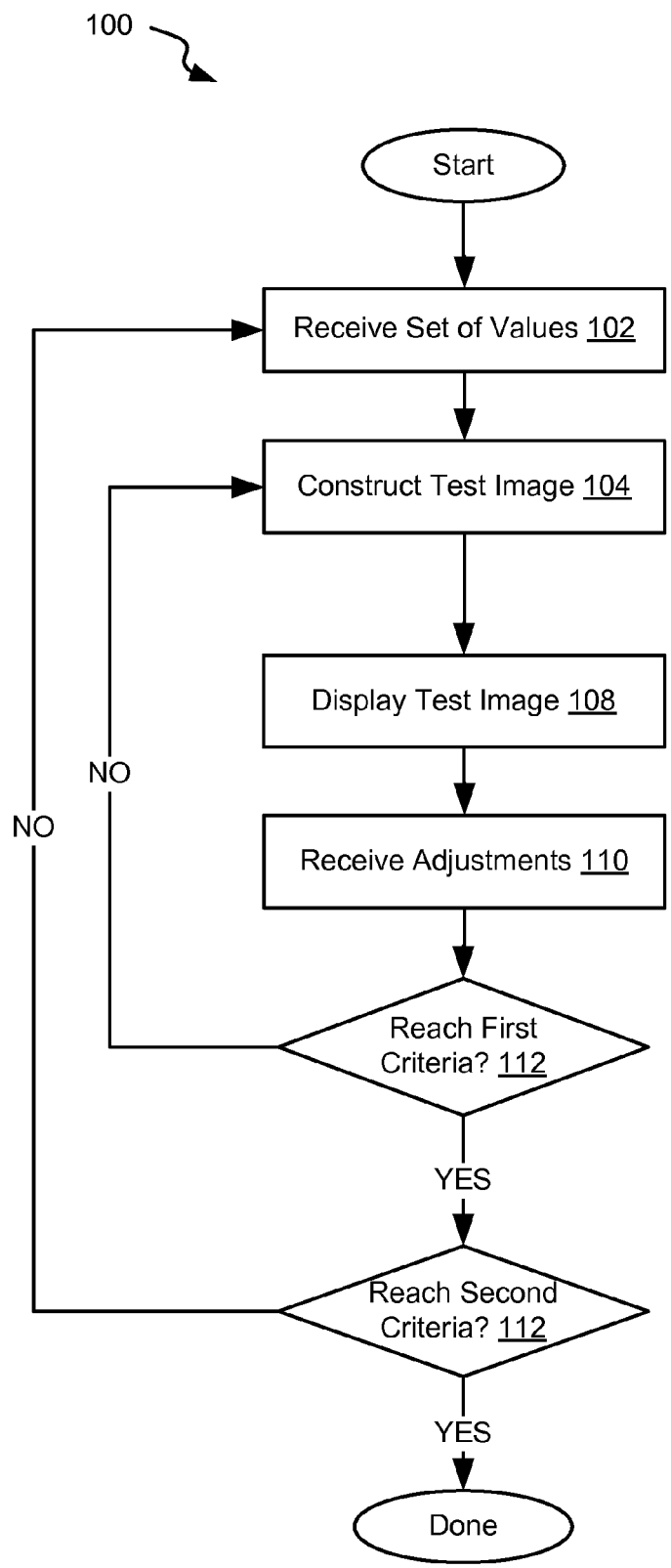
FIG. 1 is a process flowchart corresponding to one example of a technique for setting up one or more ranges of one or more inspection parameters in an optical inspection system.

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

INTRODUCTION

Solar cells and other electronic components may be inspected using an optical inspection system to determine various defects. Inspection examples include analyzing a surface for discolorations. Discoloration may be characterized using various inspection parameters, such as hue, saturation, intensity-value, and a combination thereof. Other schemes to characterize discoloration may be also used. One example is a LAB (or L*a*b*) color space, which is a color-opponent space with one dimension (L) designated for lightness and two other dimensions (A) and (B) for the color-opponent dimensions. These designations are based on nonlinearly compressed CIE XYZ (International Commission on Illumination standards) color space coordinates. Another example is YCbCr or Y'CbCr, which is a family of color spaces used as a part of the color image pipeline in optical systems. Y' is the luma component and Cb and Cr are the blue-difference and red-difference chroma components. Y' (with prime) is distinguished from Y, which is luminance. It means that light intensity is non-linearly encoded using gamma.

Some parameters may be more useful for identifying certain defects, while others may be more appropriate for other defects. For example, a saturation parameter provides strong response to certain organic and water residues (e.g., finger prints) on a solar cell surface. Yet, these residues do not impact the surface color and the hue parameter remains relatively constant. At the same time, an antireflective silicon nitride coating changes its color from light blue to dark blue, purple, and even yellow as it becomes thinner. A hue component becomes useful for thickness characterization. A hue may be also used to identify plasma stains and other types of defects.

Using multiple inspection parameters provides more granular inspection results and allows more precise differentiation among various defect categories and impact levels, e.g., critical, average, and minimal impact. These results, in turn, can be used for more accurate categorization of inspected samples, e.g., acceptable, fairly acceptable, and unacceptable. For example, solar cells are routinely categorized as A cells with critical defects taking up less than about 1% of the overall surface, B cells—1% and 5% of the surface, C cells—more than 5%, and defective cells (D cells).

Manual inspection of solar cells or a generalized approach taken in an automated system would likely make this categorization virtually impossible to implement in a robust manner. Automating this inspection process would also likely prove to be difficult. For instance, automation would entail relying on the generalizing of inspection parameters, e.g., considering an average or most predominant surface color. This type of approach may allow small, yet severe, defects to pass through undetected. Furthermore, automation may be difficult due to the complexity of inspection parameters and also entail a rather subjective nature in establishing acceptance criteria.

In novel methods and systems described herein, an inspector performs careful analysis only of a small subset of all samples, which is sometimes referred to as a training or calibration set. Using this set, an inspector identifies appropriate threshold values for one or more inspection parameters that are later used to inspect similar types of samples in an automated mode. However, even an initial set-up can be labor intensive and prone to human errors. In this regard, methods and systems described herein provide an easy-to-operate visual interface enabling an inspector to focus independently on each inspection parameter and adjust this parameter based on a displayed color representation of this parameter. The user interface allows the inspector to select any pseudo colors for these color representation and to differentiate colors depending on values of inspection parameters.

Inspection parameters may need to be set-up for each new cell type (e.g., size, coating type, fabrication parameter parameters) and inspection set-up (e.g., light sources, cameras). Therefore, a robust and user friendly set-up process can be very beneficial. A set-up may involve determining an overall range of an inspection parameter (e.g., MIN and MAX) and two or more sub-ranges within this overall range in order to be able to categorize values that correspond to this inspection parameter. For example, a saturation range may include "none positive" and "none negative" ranges that are considered desirable with respect to the imaged sample, "slight positive" and "slight negative" ranges that are less desirable but still acceptable or classified as a lesser quality cell, and "heavy" ranges that are not acceptable. If a set of saturation values corresponding to a sample contains more values that fall into the "heavy" range than is allowed by a predetermined threshold, then this sample may be deemed "rejected."

Techniques generally involve a set of values corresponding to an inspection parameter obtainable from a set-up image. For example, a color or multiple monochromatic grayscale images may be used for a discoloration analysis. These images are each viewed as a collection of set-up areas, such as pixels or sets of pixels, each with a defined value of the inspection parameter. In a discoloration analysis, each set-up area can be associated with a hue value, saturation value, and intensity value that are identified/calculated for this area. Collectively, a set-up image has one or more (e.g., three in a discoloration analysis example) sets of values. Each set of values may be analyzed independently, which allows a more focused approach to each inspection parameter.

A test image can then be constructed from multiple test areas based on corresponding set-up areas. Each test area is located in a same general position as the corresponding set-up area. In other words, each test image can correspond to the starting set-up image. However, each test area can be assigned one of the user defined colors, which are sometimes referred to as "pseudo" colors. This assignment is based on the corresponding value and user defined ranges. This arrangement provides a visual representation of the values in the set and their respective locations on the sample surface. A user interface generally includes both the range diagram and test image. A user can adjust ranges in the range diagram, which would change the test image because the same values will now fall into different ranges and corresponding pseudo colors will be shown on the test image. The process may be repeated until the test image reaches a certain predetermined criteria, which may be, for example, specific to quality of the sample used to generate the set-up image. A user may switch among multiple inspection parameters and multiple set-up images/corresponding value sets for completing the set-up.

Example Process

FIG. 1 is a process flowchart corresponding to one example of a technique for setting up one or more ranges of one or more inspection parameters in an optical inspection system. Specific implementations of this process with respect to a useful user interface are described further below. Process 100 may start with receiving a set of values corresponding to one inspection parameters in operation 102. Each of these values corresponds to a set-up area in one of set-up image. Each image is represented as a collection of areas, which may be individual pixels, combinations of pixels, or any other portions or elements of the images. Each area is assigned one or more values. The number of values depends on the number of inspection parameters used in the analysis. For example, in a discoloration analysis, each set-up area may have three values assigned to it, e.g., a hue value, saturation value, and intensity value. Therefore, each inspection parameter has a corresponding set of values representing an image.

In certain embodiments, process 100 may include one or more upstream operations that involve obtaining one or more set-up images and determining one or more sets of values corresponding to each of these images. Obtaining an image for a discoloration analysis may involve capturing at least one color image or at least three monochromatic grayscale images using a high resolution camera. A monochromatic approach entails capturing more images but may allow the use of higher resolution cameras at higher line speeds, which may not be available for color image capturing. In one monochromatic approach, an inspected sample surface is flashed with red, green, and blue (RGB) illumination (e.g., RGB LED flash lights) and at least one image is taken at each illumination color. These images are referred to as RGB monochromatic grayscale images (or simply RGB images) and generally contain the same information for discoloration inspection purposes as a single color image. It should be noted that if color images are used, they can be divided into three color components, i.e., RGB components, for further analysis. Certain details of an example optical inspection system are described further below in the context of FIG. 5.

A set-up image, whether it is a grayscale image or a color image, is represented by a collection of set-up areas. In a discoloration analysis, the images obtained using the above techniques are analyzed to obtain red (r), green (g), and blue (b) values for each set-up area. The range for each value type is zero to one (0-1). These three values (r, g, b) are then used to calculate hue (h), saturation (s), and intensity (v) values for each set-up area according to the following formulas. In certain embodiments, in order to process high resolution images at high inspection speeds, RGB and/or HSV values can be presented in an 8-bit format.

$$\max = \max(r, g, b) \quad \min = \min(r, g, b)$$

$$h = \begin{cases} 0 & \text{if } \max = \min \\ \left(60° \times \frac{g-b}{\max - \min} + 0°\right) \mod 360°, & \text{if } \max = r \\ 60° \times \frac{b-r}{\max - \min} + 120°, & \text{if } \max = g \\ 60° \times \frac{r-g}{\max - \min} + 240°, & \text{if } \max = b \end{cases}$$

$$s = \begin{cases} 0, & \text{if } \max = 0 \\ \frac{\max - \min}{\max} = 1 - \frac{\min}{\max}, & \text{otherwise} \end{cases}$$

$$v = \max$$

Returning to FIG. 1, a set of values can then be used to construct a test image in operation 104. A test image provides a visual representation of values in the set and their respective locations on the inspected surface. As noted above, a test image contains individual test areas that are positioned in the same relative locations as their corresponding set-up areas of a set-up image. A test image may be scaled up or down relative to the set-up images to provide adequate viewing on a user interface. In certain embodiments, one test area represents multiple set-up areas, in which case the corresponding values for the set-up area may be averaged.

Generally, one test image corresponds to each inspection parameter used in the set-up process. In certain embodiments, multiple test images may be constructed for one set of inspection parameters based on different sets of ranges (e.g., multiple range diagrams as further explained below). Alternatively, one image may represent multiple inspection parameters. For example, multiple values corresponding to one area may be aggregated into a single value (e.g., using a weighted average), which is then used for constructing a combined test image. This approach may be used if relative impacts on each inspection parameter are known and results can be easily combined. However, set-up granularity is lost. Creating a combined image should not be confused with presenting multiple images in the same location on the user interface in overlay, flickering-through, or other types of a collection of areas formats, which allow displaying multiple images in the same location. An example of creating a test image from a set of values will now be described in more details.

A pseudo color of each test area is determined based on the corresponding value in the set. It should be noted that the pseudo colors used for test images are provided for defect visualization purposes and typically are not representative of actual sample colors. A user may select different colors for each range in any of range diagrams that allows easier defect differentiation. In order to determine a color for a test area, the corresponding value is compared to the ranges identified for these inspection factors. These ranges can be displayed on a range diagram further described below. Ranges are sometimes referred to as "bands" as they can be represented by colored bands in a range diagram. For example, a range diagram may have two ranges identified, e.g., an "acceptable" range that has green color assigned and an "unacceptable" range that has red color. If a value falls within the "acceptable" range, then the corresponding test area takes green color assigned. Alternatively, if the value falls within the "unacceptable" range, then this test area takes on a red color. This operation can be repeated for all values in the set, until the entire image includes only green or red test areas.

When a complete test image is displayed on a user interface, a user can assess how many values fall in each range and which areas of the sample have areas that fall, for example, into the "unacceptable" range. This image not only provides visual representation of how defective the sample is (e.g., how much red is on the surface), but it also indicates defect distribution. It should be also noted that three or more ranges and corresponding colors may be used to further characterize levels of defects. These ranges are explained in more details below.

Process 100 may continue with displaying one or more test image together with one or more range diagrams on a user interface of the optical inspection system in operation 108. Typically, each range diagram corresponds to one inspection parameter and includes two or more threshold limits defining multiple ranges. However, in certain embodiments mentioned above, one test image may be used to represent multiple inspection parameters and controlled by multiple range diagrams.

Figure 2A:
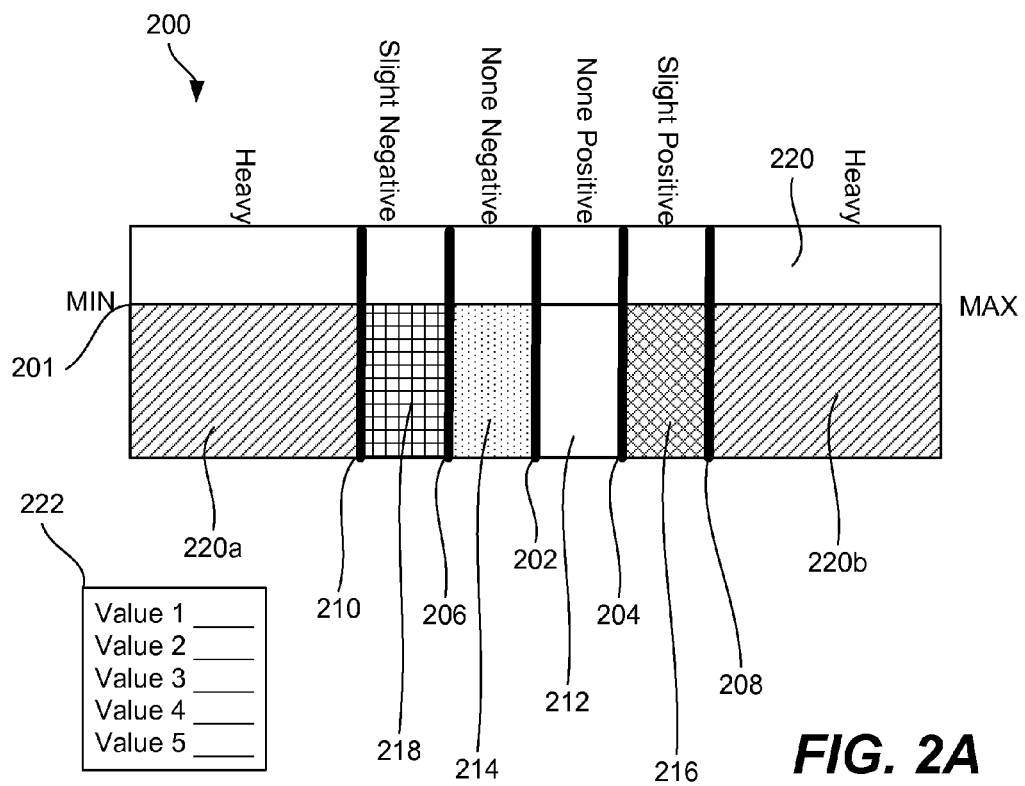
FIG. 2A is a schematic representation of a range diagram in accordance with certain embodiments.

FIG. 2A is a schematic representation of a range diagram 200 in accordance with certain embodiments. This diagram may be used by the user to control threshold limits and ranges. In certain embodiments, the diagram extends from a MIN limit on the left to a MAX limit on the right. A MIN limit may be pre-set to zero (as in the examples described above) or any other value that is less than a MAX limit. A MAX limit may be preset to one (as in the examples described above) or any other value that is more than a MIN limit. In certain embodiments further described in the context of FIG. 2C, a circular diagram is used to represent circular parameters such as hue. In this type of diagrams, MIN and MAX limits may coincide at the same radius (i.e., 0° and 360° in a hue circle).

A range between the MIN and the MAX limits is referred to as an "overall range". This overall range can be divided into two or more smaller ranges by threshold limits, which are also referred to herein as handles. In a specific implementation, at least two limits are used to define a middle range and two outside ranges. In an example illustrated in FIG. 2A, five handles 202, 204, 206, 208, and 210 are used to define six ranges 212, 214, 216, 218, 220*a*, and 220*b*. Each handle/limit has a corresponding value that determines position of this handle in the overall range. For a first iteration of the process 100, a set of default values may be used or set according to different algorithms described below. These limits may be adjusted as further described below by a user by either dragging handles left or right with a pointing device, providing numerical inputs into dialog box 222, or via some other type of input interface.

One handle (e.g., the center handle), such as handle 202 in FIG. 2A, may be associated with a nominal value/limit, or simply a nominal limit. A nominal limit can be calculated from a set of values for this inspection parameter. A new nominal limit may be automatically determined from each new set. This allows using a nominal limit as a reference that makes measurement relative to each other. A nominal limit may represent a mean or median value of the entire set of values or a subset of the entire set. For example, in case of hue, a nominal limit may represent the most common color of the inspected surface. Other algorithms may be used to determine a nominal limit.

Other limits may be used in addition or instead of the nominal limit. In certain embodiments, an optical system is configured to preserve, at least initially, a relationship between ranges. For example, distances between some or all limits/handles (i.e., range widths) may be maintained constant. In these embodiments, when a nominal limit is adjusted for a new set of values, all other limits are shifted accordingly. In other embodiments, initial positions of limits may follow a certain statistical distribution (e.g., a nominal limit corresponds to an average value, while other limits coincide with standard deviations).

Limits define ranges within the overall range. Multiple ranges may be referenced with various naming conventions. Generally, a range to the right of the nominal value 202 may be referred to as a first range 212, while a range to the left of the nominal value 202 may be referred to as a first opposite range 214. A range to the right of the first range 212 may be referred to as a second range 216, while a range to the left of the first opposite range may be referred to as a second opposite range 218, and so on. It should be noted that the first range 212 and the first opposite range 214 may have the same or different width (e.g., numerical difference between two limits defining a range). Furthermore, the first range and the second range may have the same or different widths.

Figure 2B:
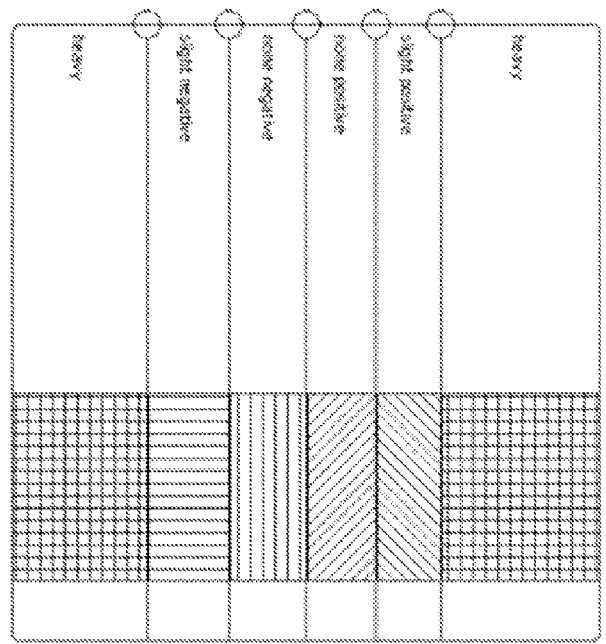
FIG. 2B illustrates one example of a range diagram representing a linear inspection parameter, such as intensity-value or saturation.
Figure 2C:
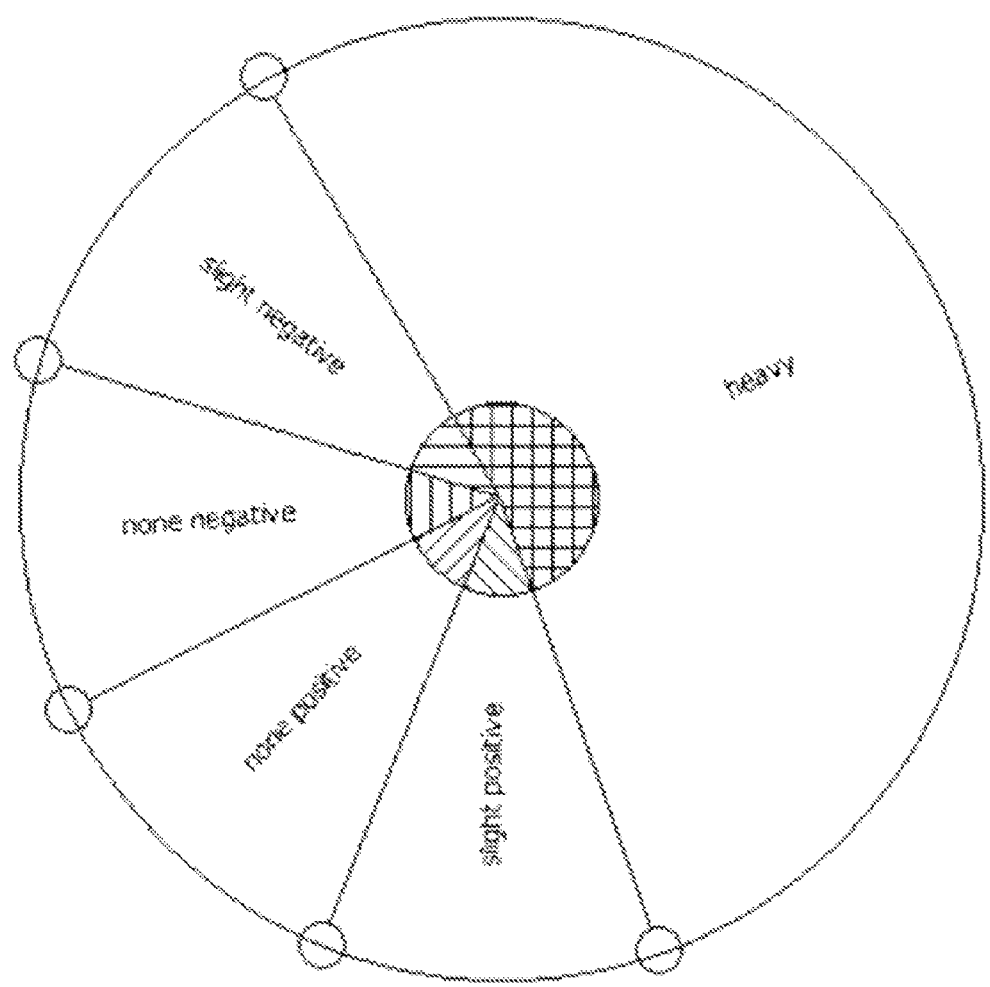
FIG. 2C illustrates another example of a range diagram representing a circular inspection parameter, such as hue.

Another naming scheme is illustrated in FIGS. 2B and 2C. Analogizing to elements of FIG. 2A, two ranges 204 and 206 on each side of the nominal limit defined by handle 202 are called "none positive" and "none negative," respectively, and may represent acceptable values. Two ranges 216 and 218 further separated from the nominal limit defined by handle 202 are called "slight positive" and "slight negative," respectively, and may represent still acceptable values but less desirable that ones falling within the previous two ranges. Finally, two outside ranges 220*a* and 220*b* that complete the overall range are called "heavy" and may represent unacceptable values.

In order to visualize present values in the set and locations of the corresponding set-up areas, ranges are assigned different colors. Although shown in grayscale in the illustrated figures, colors would typically be displayed in the range diagrams (and other images) in preferred embodiments. For example, a range 212 may be assigned blue color, a range 214 may be assigned green color, a range 216 may be assigned red color, a range 218 may be assigned a blue color, and both outside ranges 220a and 220b may be assigned a yellow color. These colors are used to constructs a test image as explained below in the context of FIG. 3. A user interface allows reassigning colors corresponding to ranges, which would lead to new colors being displayed in a corresponding test image.

Range diagram 200 may also include a visual bar 220 to assist users with understanding representation of corresponding values in the range. For example, a visual bar for a hue range diagram may be a color circle (or a color bar) indicating specific colors corresponding to each limit/handles. For intensity and saturation range diagrams, visual bars may be gray scales changing from white to black.

FIG. 2B illustrates one example of a range diagram that could be used for a linear inspection parameter, such as intensity or saturation. FIG. 2C illustrates another example of a range diagram that could be used for a circular inspection parameter, such as hue. It should be noted that a hue parameter may also be controlled with a linear range diagram in which a linear visual bar line representing a circumference of the color circle extending from 0° to 360°.

Figure 3:
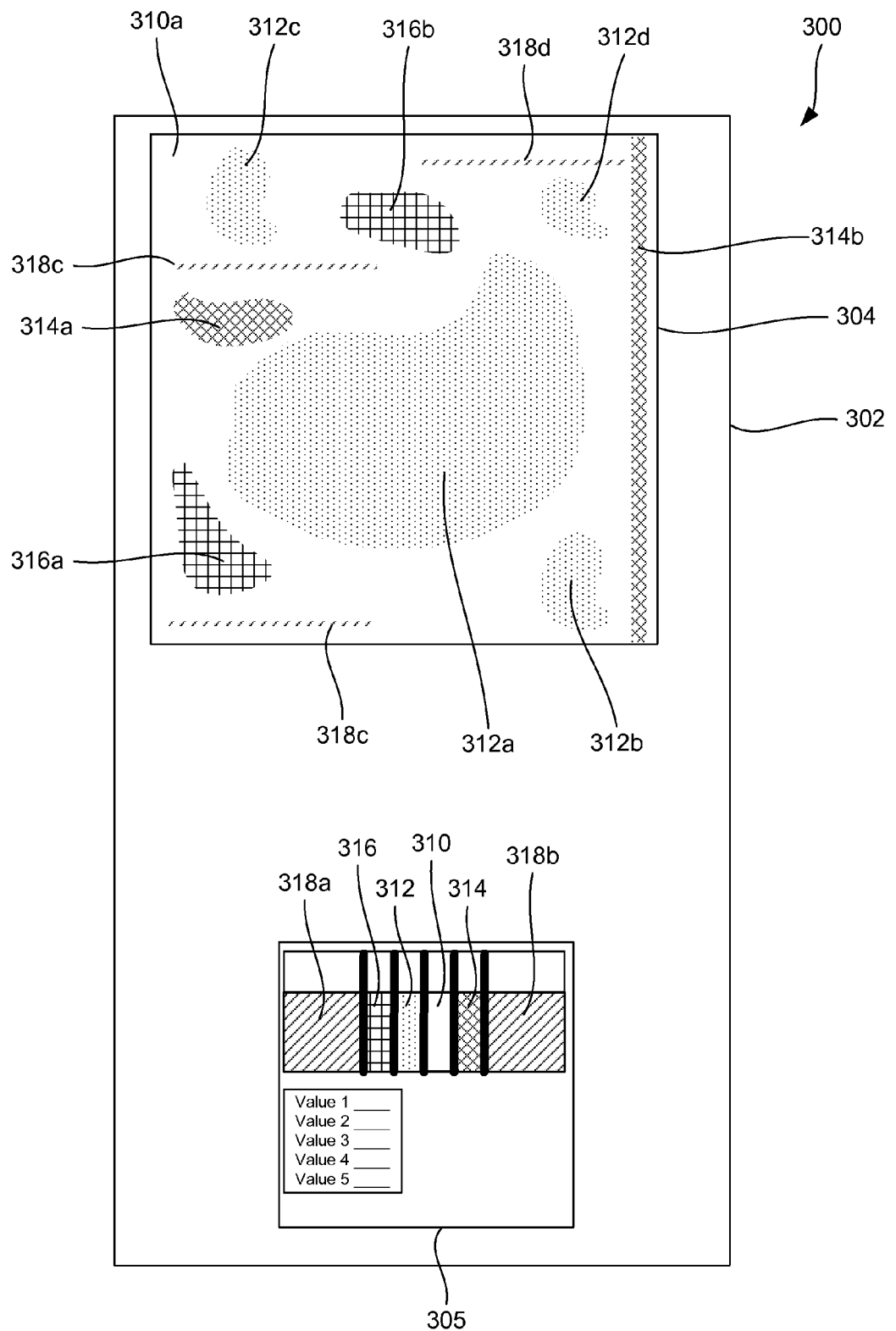
FIG. 3 illustrates schematic representations of a user interface containing a test image and range diagram in accordance with certain embodiments.

FIG. 3 is a schematic representation of user interface 302 displaying test image 304 and range diagram 305 in accordance with certain embodiments. A user interface may display one test image—range diagram combination at one time as shown in FIG. 3. For example, each inspection parameter may have a designated tab on the screen for displaying corresponding test images and range diagrams. In other embodiments, all range diagrams and test images are displayed on the same screen allowing a user to compare test images corresponding to different inspection parameters. Furthermore, in certain embodiments, a test image may be displayed as an overlay over the corresponding set-up image. In yet other embodiments, multiple test images may be displayed for short periods of time in the same area of the user interface creating a flickering effect.

A test image is constructed from test areas that have assigned colors (e.g., 310a, 312a-c, 314a-b, 316a-b, and 318c-d) based on the corresponding values in the set. (Although not shown in the illustrated figures, the test image preferably includes differently colored test areas). This test image indicates that certain values in the corresponding set from the imaged sample fell into the first range 310 of the range diagram 305, which resulted in un-shaded area 310a. The color of this area corresponds to the user defined color of range or area 310. Furthermore, some values in the set fell into the second range 312, which results in three dotted areas 312a-c shown in the test image. Other values fell into the third range 314 resulting in two shaded areas 314a-b. Yet other values fell into the fourth range 316 resulting in two other shaded areas 314a-b. Finally, the remaining value must have fell into the outside ranges 318a-b resulting in the shaded areas 318c-d. Collectively all these areas 310, 312a-c, 314a-b, 314a-b, and 318c-d make up the test image 304.

In certain embodiment, a user interface may have an area (not shown) for displaying numerical results that indicate how much area is designated for each color. These ratio values also represent how many of all values in a set fall into each of the range. These values can be used as an objective standard during set-up and later during inspection.

Returning to FIG. 1, process 100 may continue with receiving adjustments to one or more limits in the range diagram in operation 110. Adjustments may be performed by entering new numerical values in the dialog box (e.g., dialog box 222 in FIG. 2A), using scroll arrows in the dialog box to move up or down the value list, or moving handles on the range diagram with a user input device. In certain embodiments, minimum predefined gaps between handles are set such that when one handle is moved too close to another handle, the other handle starts moving together with the first handle. This feature prevents switching of handles if one is moved too far.

In certain embodiments, specific relationships are established between handles. For example, position of handles may be locked relative to each other such that the range is maintained if one of the handles is moved. Furthermore, widths of ranges may relate to each other such that changing a width of one range will automatically change a width of another. These relationships may cause one or more limits to fall outside of the overall range. While the limits/handles are not visible anymore, ranges established by these limits may still be used.

Figure 4A:
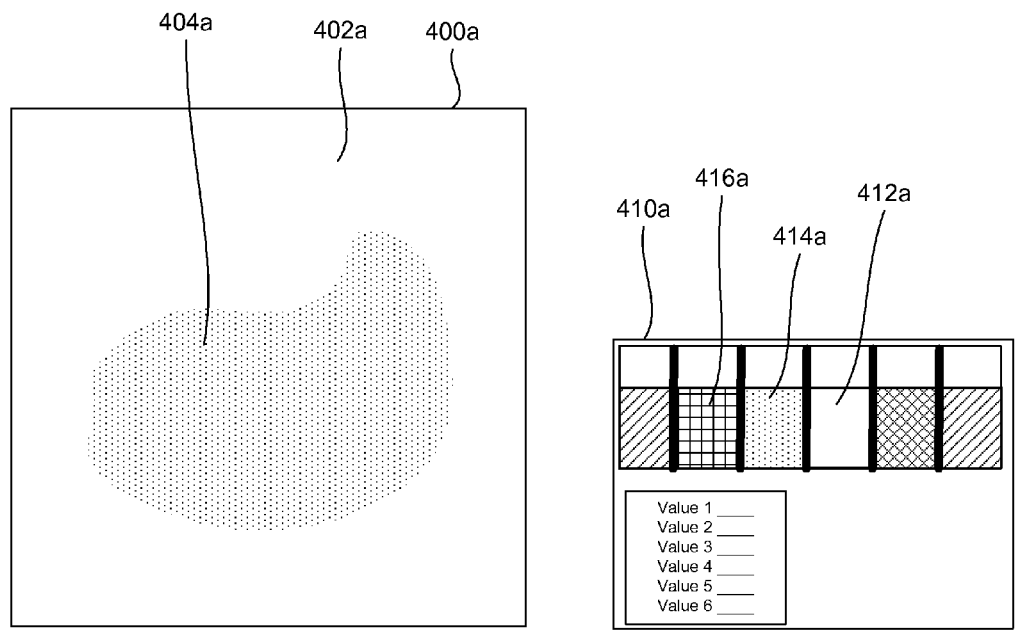
FIGS. 4A and 4B are schematic representations of a test image and corresponding range diagram illustrating changes in the test image based on different range settings in the range diagram.
Figure 4B:
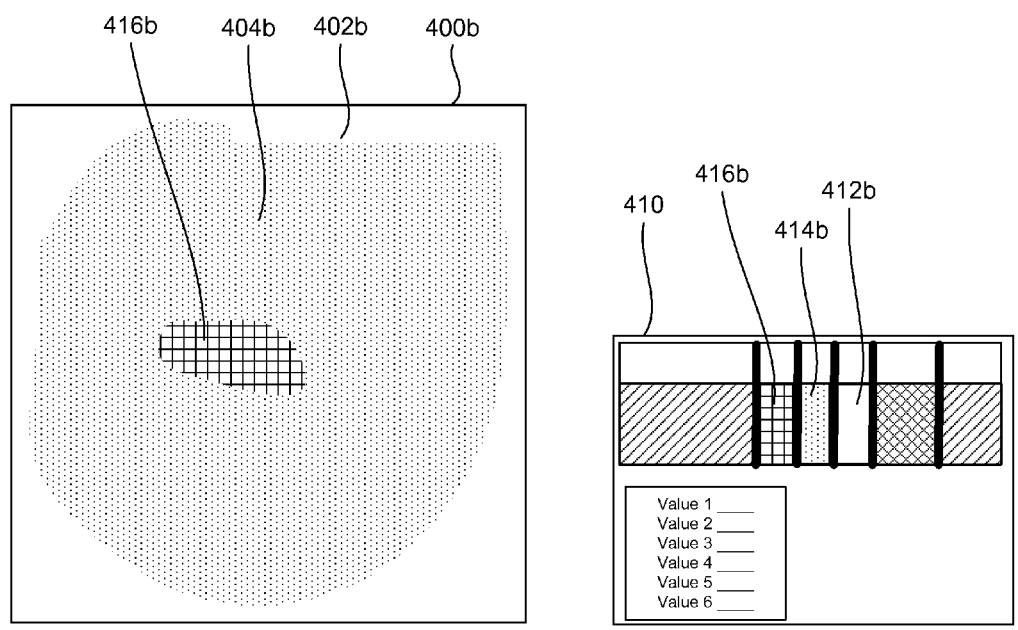

FIGS. 4A and 4B are schematic representations of a test image and corresponding range diagram showing illustrating changes in the test images based on different range settings in the range diagram. It should be noted that both views 400a and 400b of the test image correspond to the same set of values provided from the set-up image. FIG. 4A shows that range diagram 410a has relative wide ranges 412a, 414a, and 416a. Values in the set fell predominantly into range 412a leading to un-shaded area 402a on the test image. The rest of the values fell into range 414a leading to smaller dotted area 404a. A used may decide that this view 400a of the test image does not adequately represent the inspected sample. For example, there may be a small discoloration area in the middle of the sample that is not adequately presented in this test image view 400a. As such, a user may adjust limits in the range diagram 410 to come up with new narrower ranges 412b, 414b, and 416b. Some of the values in the set still fall into range 412b leading to un-shaded area 402b. However, because range 412b is narrower, fewer values fall within this range, leading to smaller un-shaded area. Some values may fall into range 414b. However, some values now fall into range 416b leading to cross-hatched area 416b. As provided in the above example, this area 416b may now be representative of the discoloration in the middle of the sample. In other words, a user performed an adjustment to set up more appropriate ranges for this inspection parameter.

This operation of constructing and displaying new test images and receiving adjustments may be repeated until the test image reaches predetermined criteria (e.g., in operations 112).

Apparatus

Figure 5:
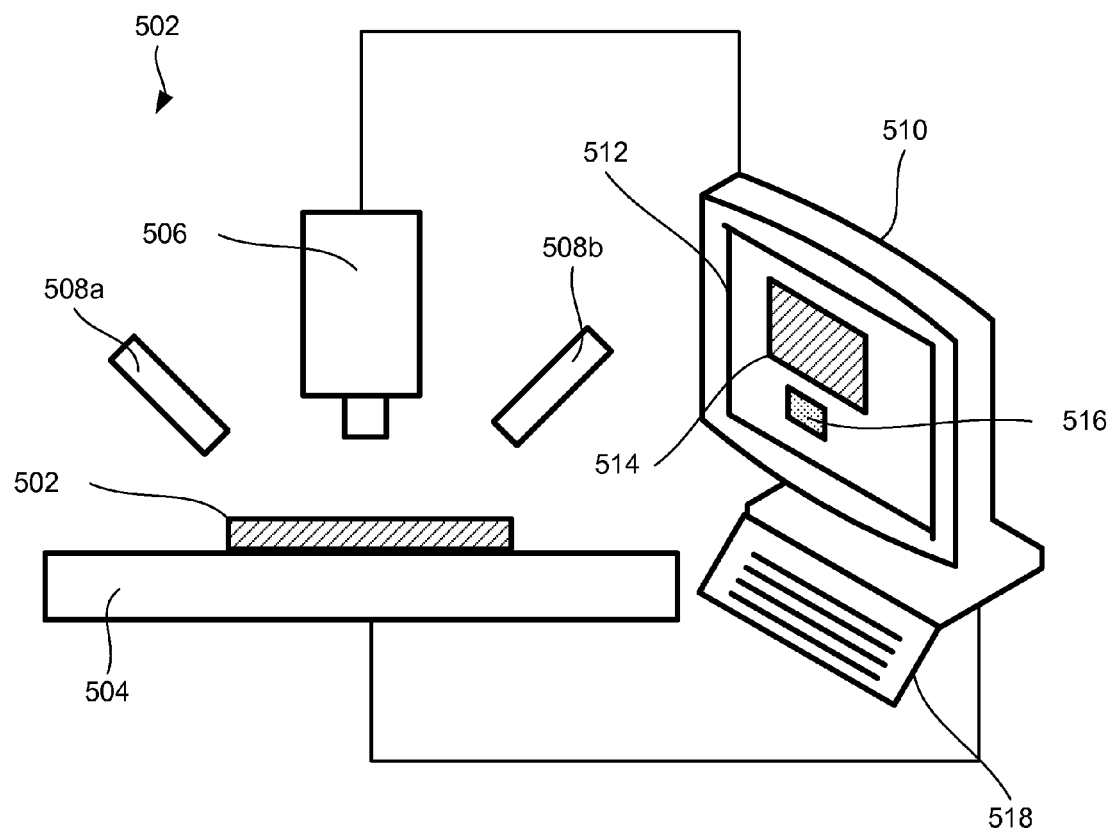
FIG. 5 is a schematic representation of an optical inspection system in accordance with certain embodiments.

FIG. 5 is a schematic representation of an optical inspection system 500 in accordance with certain embodiments. Such a system could be used for implementation of techniques described in context of FIG. 1. One example of suitable inspection systems is the "PVI-6 Wafer and Cell Inspection System" available from KLA Tencor in San Jose, Calif.

System 500 may include stage 504 for holding up a sample 502. Stage 504 may be integrated with an autoloader for automatically delivering and removing samples from the stage. High resolution camera 506 is focused on a surface of sample 502. In certain embodiments, a camera is configured to capture an image of the entire sample surface. In other embodiments, an X-Y moving stage may be used to provide multiple relative positions of the camera to the sample and/or move one with respect to another at a predetermined speed to scan the surface of the sample. Furthermore, system 500 may also include one or more light sources, e.g., 508a-b, for illuminating the inspected surface.

Camera 506 is typically connected to computer system 510 to transmit data corresponding to set-up images. Computer system 510 is configured (e.g., with programming instructions) to provide interface 512 (e.g., a computer screen) for displaying test image 514 and range diagram 516. Computer system 510 may also include one or more input devices 518 (e.g., a keyboard, mouse, joystick) for providing input from the user such as changing limits and assigning new colors. Computer system 510 may also be connected to stage 504 for controlling, for example, a sample position (focusing and scanning) and other elements of the system. In certain embodiments, computer system 510 is configured to carry out set up techniques detailed above. For example, computer system 510 may be used to generate one or more set-up value sets from a set-up image. Additionally, computer system 510 may be used for constructing test images and displaying the test images and corresponding range diagrams. Finally, computer system 510 may be used to receive adjustments to the range diagrams. Computer system 510 typically has one or more processors coupled to input/output ports, and one or more memories via appropriate buses or other communication mechanisms.

Because such information and program instructions may be employed to implement the systems/methods described herein, the present invention relates to machine readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

CONCLUSION

Although the foregoing invention has been described in some detail for purposes of clarity of understanding, it will be apparent that certain changes and modifications may be practiced within the scope of the appended claims. It should be noted that there are many alternative ways of implementing the processes, systems and apparatus of the present invention. Accordingly, the present embodiments are to be considered as illustrative and not restrictive, and the invention is not to be limited to the details given herein.

What is claimed is:

1. A method for setting up one or more ranges of one or more inspection parameters in an optical inspection system, the method comprising:
   (a) receiving a set of values of an inspection parameter, wherein the set of values corresponds to set-up areas of a set-up image obtained from a sample;
   (b) constructing a test image comprising multiple test areas such that locations of the test areas corresponds to locations of the set-up areas and such that colors of the test areas are determined by corresponding values in the set;
   (c) displaying the test image and a range diagram on a user interface of the optical inspection system,
      wherein the range diagram corresponds to the inspection parameter and comprises a nominal limit and a variation limit,
      wherein the nominal limit and the variation limit define a range corresponding to a color that does not overlap with an outside range corresponding to an outside color, and
      wherein the test areas have the color if the corresponding values in the set fall within the range or the outside color if the corresponding values fall within the outside range;
   (d) receiving an adjustment of the variation limit and/or the nominal limit based on the test image;
   (e) repeating (b)-(d) until the test image reaches predetermined criteria;
   (f) receiving a second set of values of a second inspection parameter,
      wherein the inspection parameter and the second inspection parameter are different types of inspection parameters,
      wherein the second set of values corresponds to the set-up areas of the set-up image or a second set-up image obtained from the sample;
   (g) constructing a second test image comprising multiple second test areas such that locations of the second test areas corresponds to location of the set-up areas and such that colors of the second test areas are determined by determined by corresponding values in the second set;
   (h) displaying the second test image and a second range diagram on the user interface of the optical inspection system,
      wherein the second range diagram corresponds to the second inspection parameter and comprises a second nominal limit and a second variation limit,
      wherein the second nominal limit and the second variation limit define a second range corresponding to a second color that does not overlap with a second outside range corresponding to a second outside color, and
      wherein the second test areas have the second color if the corresponding values in the second set fall within the second range or the second outside color if the corresponding values fall within the second outside range;
   (i) receiving an adjustment of the second variation limit and/or the second nominal limit based on the second test image;
   (j) repeating (f)-(i) until the second test image reaches predetermined criteria; and
   (k) setting two or more ranges for the inspection parameter and the second inspection parameter in the optical inspection system based on the variation limit and the nominal limit corresponding the test image at the predetermined criteria and based on the second variation limit and the second nominal limit corresponding the second test image at the predetermined criteria.

2. The method of claim 1, wherein the predetermined criteria is a balance between the color and the outside color relative to a level of defects present on a sample corresponding to the set-up image.

3. The method of claim 1, wherein the set-up image is obtained from a photovoltaic cell.

4. The method of claim 1, wherein the inspection parameter is a measure of discoloration.

5. The method of claim 1, wherein the inspection parameter is selected from the group consisting of hue, saturation, and intensity.

6. The method of claim 1, further comprising calculating the set of values from corresponding RGB values obtained from the set-up images.

7. The method of claim 1, further comprising obtaining the set-up image from a set-up sample.

8. The method of claim 1, further comprising receiving multiple sets of values of the inspection parameter, wherein the multiple sets of values corresponding to multiple set-up images having varying defect levels.

9. The method of claim 1, wherein the set-up areas are individual pixels of the set-up image.

10. The method of claim 1, wherein the range diagram comprises a diagram selected from the group consisting of a hue circle, a saturation spectrum, and an intensity spectrum.

11. The method of claim 1, wherein the nominal limit is initially set to the most common of all values in the set.

12. The method of claim 1, wherein a spread of the range remains the same when adjusting the nominal limit or the variation limit.

13. The method of claim 1, wherein receiving the adjustment comprises receiving a numerical input and/or performing a graphical adjustment of the variation limit and/or the nominal limit on the range diagram.

14. The method of claim 1, wherein the user interface is configured to allow a user to assign other colors to the range and the outside range.

15. The method of claim 1, further comprising inspecting one or more additional samples using the inspection parameter and the second inspection parameter in an automated mode using the two or more ranges for the inspection parameter and the second inspection parameter.

16. The method of claim 1, wherein the inspection parameter is hue, and wherein the second inspection parameter is saturation value.

17. The method of claim 1, wherein the second set of values corresponds to the set-up areas of the set-up image.

18. An optical inspection system for setting up one or more ranges of one or more inspection parameters, comprising at least one memory and at least one processor that are configured to perform the following operations:
 (a) receiving a set of values of an inspection parameter,
   wherein the set of values corresponds to set-up areas of a set-up image obtained from a sample;
 (b) constructing a test image comprising multiple test areas such that locations of the test areas corresponds to locations of the set-up areas and such that colors of the test areas are determined by corresponding values in the set;
 (c) displaying the test image and a range diagram on a user interface of the optical inspection system,
  wherein the range diagram corresponds to the inspection parameter and comprises a nominal limit and a variation limit,
  wherein the nominal limit and the variation limit define a range corresponding to a color that does not overlap with an outside range corresponding to an outside color, and
  wherein the test areas have the color if the corresponding values in the set fall within the range or the outside color if the corresponding values fall within the outside range;
 (d) receiving an adjustment of the variation limit and/or the nominal limit based on the test image; and
 (e) repeating (b)-(d) until the test image reaches predetermined criteria;
 (f) receiving a second set of values of a second inspection parameter,
  wherein the inspection parameter and the second inspection parameter are different types of inspection parameters,
  wherein the second set of values corresponds to the set-up areas of the set-up image or a second set-up image obtained from the sample;
 (g) constructing a second test image comprising multiple second test areas such that locations of the second test areas corresponds to location of the set-up areas and such that colors of the second test areas are determined by determined by corresponding values in the second set;
 (h) displaying the second test image and a second range diagram on the user interface of the optical inspection system,
  wherein the second range diagram corresponds to the second inspection parameter and comprises a second nominal limit and a second variation limit,
  wherein the second nominal limit and the second variation limit define a second range corresponding to a second color that does not overlap with a second outside range corresponding to a second outside color, and
  wherein the second test areas have the second color if the corresponding values in the second set fall within the second range or the second outside color if the corresponding values fall within the second outside range;
 (i) receiving an adjustment of the second variation limit and/or the second nominal limit based on the second test image;
 (j) repeating (f)-(i) until the second test image reaches predetermined criteria; and
 (k) setting two or more ranges for the inspection parameter and the second inspection parameter in the optical inspection system based on the variation limit and the nominal limit corresponding the test image at the predetermined criteria and based on the second variation limit and the second nominal limit corresponding the second test image at the predetermined criteria.

* * * * *